United States Patent [19]

Sano et al.

[11] 4,402,820

[45] Sep. 6, 1983

[54] OXYGEN ANALYZER

[75] Inventors: Hiromi Sano, Nagoya; Masatoshi Suzuki, Anjo; Masaya Fujimoto; Mitihiro Yamakawa, both of Kariya; Toshitaka Saito, Toyohashi, all of Japan

[73] Assignee: Nippondenso, Co., Ltd., Kariya, Japan

[21] Appl. No.: 403,045

[22] Filed: Jul. 29, 1982

[30] Foreign Application Priority Data

Aug. 5, 1981 [JP] Japan ................ 56-123373

[51] Int. Cl.$^3$ .................. G01N 27/56; G01N 27/58
[52] U.S. Cl. .................................. 204/425; 204/429
[58] Field of Search ................ 204/425, 429, 15

[56] References Cited

U.S. PATENT DOCUMENTS 4,265,930 5/1981 Shinohara et al. ............ 204/429 X

FOREIGN PATENT DOCUMENTS 2711880 9/1978 Fed. Rep. of Germany ...... 204/429

Primary Examiner—G. L. Kaplan
Attorney, Agent, or Firm—Cushman, Darby & Cushman

[57] ABSTRACT

A limiting current type oxygen analyzer designed for detecting oxygen concentration comprising a solid electrolyte element made from an oxygen ion conductive metal oxide and a pair of porous film electrodes provided on the inner and outer sides of said element respectively, at least one side electrodes being coated with a gas-diffusive resistive layer made from a porous insulating metal oxide, wherein the oxygen ions in the gas to which said element is exposed are caused to diffuse in the inside of said electrolyte element by applying a given voltage across said both electrodes and the limiting current corresponding to the concentration of said diffused oxygen ions is measured to determine the oxygen concentration in the gas to be analyzed, further characterized in that said gas-diffusive resistive layer is composed of a three-layer structure consisting of the first, second and third layers counted from the electrode side, said first layer having porosity of 11–15%, the second layer 6–8% and the third layer 15–20%.

4 Claims, 7 Drawing Figures

OXYGEN ANALYZER

This invention relates to a limiting current type oxygen analyzer.

The conventional oxygen analyzers of this type are basically of a structure in which porous film electrodes are provided on the inner and outer sides, respectively, of a solid electrolyte element made from an oxygen ion conductive metal oxide see, for example, Japanese Patent Kokai (Laid-Open) No. 116896/78].

In use of these analyzers, a voltage is applied across both electrodes to cause a current flow from one electrode to the other. Since said element is an oxygen ion conductive solid electrolyte, oxygen in the gas to be analyzed turns into oxygen ions upon receiving electrons from one of the electrodes, and these oxygen ions diffuse in said element to reach the other electrode. Upon reaching this latter electrode, said oxygen ions release electrons to return into oxygen molecules. This cycle of movements causes a current flow between both electrodes. In the course of such pattern of actions, there is created a region where the strength of the current flowing between the electrodes remains unchanged even if the voltage applied is varied, that is, a limiting current is generated. Therefore, by measuring such limiting current generated when a predetermined voltage was applied across both electrodes, it is possible to know the oxygen concentration in the gas to be analyzed.

This type of oxygen analyzers, however, involve some serious problems: there is a possibility that the electrodes might come off the electrolyte element surfaces due to the gas temperature changing cycle if said electrodes are left exposed directly to the gas to be analyzed, and also oxygen in the gas to be analyzed may fail to diffuse effectively in said solid electrolyte element. As a measure against this, there is generally employed the idea of coating the electrode surface with a gas-diffusive resistive layer made from a porous insulating metal oxide. In the oxygen analyzer using such gas-diffusive resistive layer, said limiting current $I_l$ is calculated from the following formula (1):

$$I_l = \frac{4F \cdot DO_2}{R \cdot T} \cdot \frac{E}{L} \cdot S \cdot PO_2 \tag{1}$$

wherein
F: Faraday's constant
R: Gas constant
$DO_2$: Diffusion constant of oxygen molecules
T: Absolute temperature
E: Diffusivity of gas-diffusive resistive layer
L: Effective diffusion length of the gas-diffusive resistive layer
S: Electrode surface area
$PO_2$: Partial pressure of oxygen It is thus noted that the limiting current $I_l$ is influenced by diffusivity E and effective diffusion length L of said gas-diffusive resistive layer.

In the conventional oxygen analyzers, however, said gas-diffusive resistive layer coating the electrode surface is formed from a single composition, so that such layer is liable to get clogged up with dust existing in the gas to be analyzed, resulting in an increased resistance to gas diffusion in said layer and a reduced value of limiting current. This warps the measurements of oxygen concentration.

In order to overcome the said defects in the conventional oxygen analyzers, the present invention adopts a three-layer structure for said gas-diffusive resistive layer, with the respective sub-layers being varied in porosity from each other, thereby to inhibit clog-up of said resistive layer to minimize the fluctuation of limiting current density, thus allowing correct measurement of oxygen concentration.

The present invention is now described in detail with reference to the accompanying drawings.

Figure 1A:
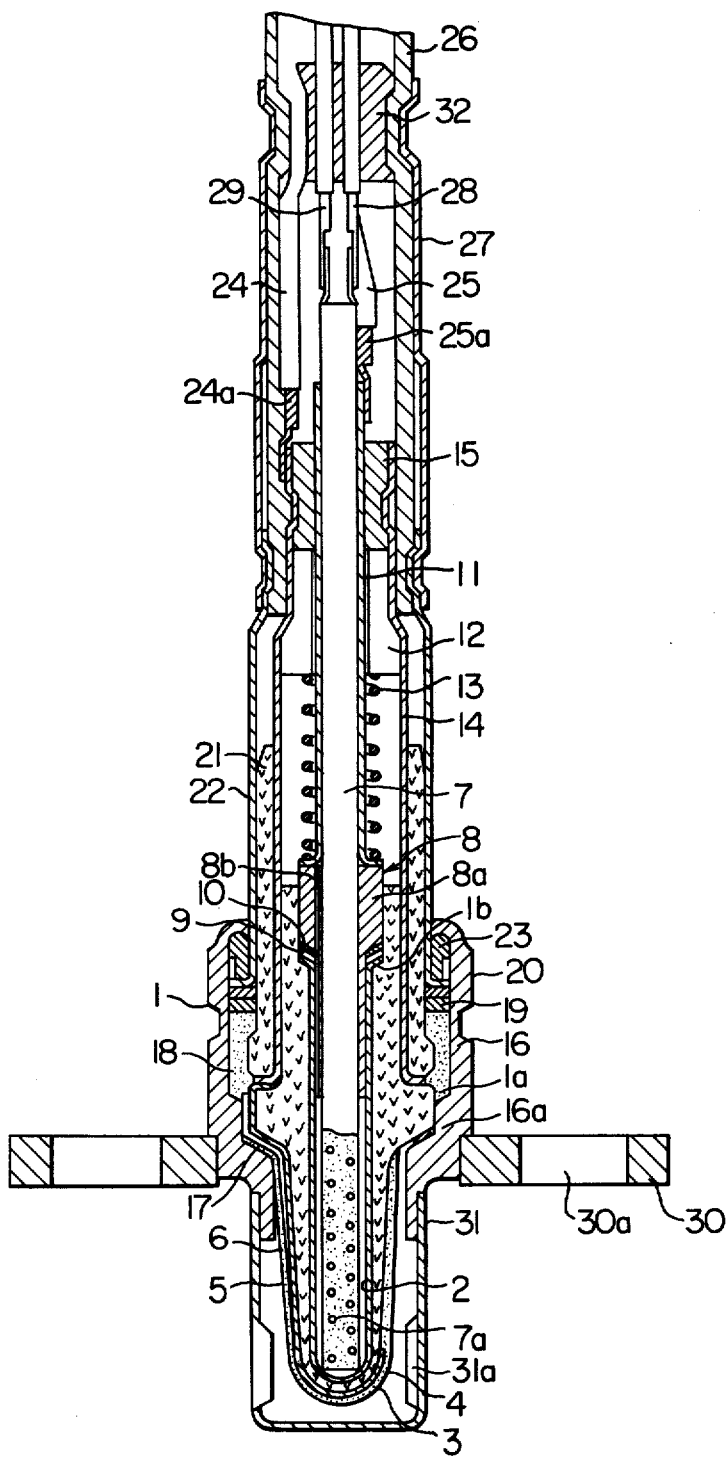
FIG. 1(a) is a sectional view of an oxygen analyzer embodying the present invention.

In the drawings, the following nomenclature is used to indicate the essential parts of the device:
1: solid electrolyte element; 2, 3: electrodes; 4: gas-diffusive resistive layer; 4a: first layer; 4b: second layer; 4c: third layer.

Figure 1B:
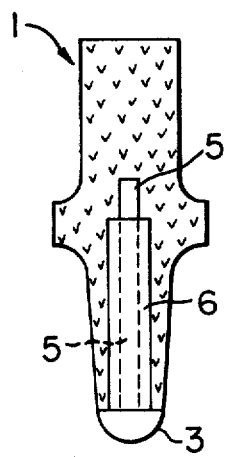
FIG. 1(b) is a frontal view of the element portion in the analyzer shown in FIG. 1(a).
Figure 2:
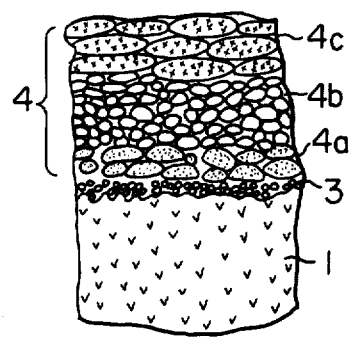
FIG. 2 is a schematic sectional view of the principal parts of the analyzer of FIG. 1(a).

Referring to FIG. 1, numeral 1 designates a solid electrolyte element made of a dense sintered body of a solid solution comprising 90-95 mol% of $ZrO_2$ and 5-10 mol% of $YbO_3$ or $Y_2O_3$. This element 1 is of a cup-like configuration closed at its one end and open at its other end. The central part of the element 1 bulges out to form the annular enlarged portion 1a, and an annular seat 1b is provided at the open end in the inner periphery thereof. Numeral 2 denotes a film-like porous platinum electrode provided inside of the element 1, said electrode 2 extending along substantially the entire length of the element, reaching said seat portion 1b. A similar film-like porous platinum electrode 3 is also provided at the closed end of the element 1. This porous platinum electrode 3 is designed to have a surface area of 5 to 100 mm². The portion of the element 1 where said electrode 3 is provided has a thickness of 0.5 mm. Numeral 5 connotes an electrode lead wire which is also made of platinum. Said lead wire 5 is provided on one side of the element 1 in electrical connection to the electrode 3. The terminal end of said lead wire 5 reaches the top face of the annular enlarge portion 1a of the element 1. Any suitable method such as chemical plating, paste screen printing, etc., may be used for installing said lead wire 5 and electrodes 2 and 3 in the element 1. Provided on the lead wire 5 is a high-melting-point glass coating 6 imprevious to gas, said coating 6 being adapted for keeping the sensor safe from any influence of a false current. Said glass coating 6 extends to the annular enlarged portion 1a of the element 1, that is, to the position not obstructing contact and electrical connection of the lead wire 5 with the cover 14. Numeral 4 indicates an oxygen-diffusive resistive layer which features the present invention. This layer 4 is of a composite structure consisting of three sub-layers 4a, 4b and 4c as shown in FIG. 2. The first layer 4a overlying the electrode 3 is made from $ZrO_2$. This layer 4a has little or no difference in thermal expansibility from the element 1 and is provided for bettering adhesion of the gas-diffusive resistive layer 4 to the electrode 3. In the limiting current system oxygen analyzer according to this invention, the analyzer characteristics are governed by the electrode 3 which has only a small surface area, so that the first layer 4a is provided for eliminating any risk of separation of the composite layer 4 in long-time use. Said first layer 4a is a rather porous coating film with a porosity of 11 to 15% and has a thickness of 20 to 50 microns.

The second layer 4b overlying the first layer 4a is a layer composed of a spinel $MgO.Al_2O_3$. This is an important component which decides the limiting current characteristics of the analyzer and is formed from a dense coating film having a thickness of 130 to ;b 160 microns and a porosity of 6 to 8%. Lying above said second layer 4b is the third layer 4c formed from $Al_2O_3$ and having a thickness of 130–160 microns. This is a very porous coating film with a porosity of 15 to 20%. This third layer 4c is made highly porous for the purpose of preventing the layer assembly 4 from being clogged up with the deposits (various kinds of compounds of Pb, P, S, Ca, Zn, Ba, etc.) which build up in long-time use and is intended to keep off any external influence to the second layer 4b, that is, to bar out any factor liable to cause a change of the limiting current characteristics of the analyzer. These three layers 4a, 4b and 4c are formed by plasma spray coating to a coating thickness of approximately 200 microns as a whole, and such three layers of said thickness are provided at least on the electrode 3. Only a single-layer coating may be provided on other parts than the electrode 3.

Again referring to FIG. 1, numeral 7 denotes an elongated bar-shaped ceramic heater comprising a coiled or comb-shaped heater wire 7a such as michrome wire housed in, for example, alumina porcelain. Numeral 8 refers to a metallic pipe provided with a flange 8a and a through-hole 8b. This pipe 8 is fitted around said heater 7 and joined thereto by silver soldering or other means. Said pipe 8 has its flange 8a positioned on the annular seat 1b of the element 1 through the media of a ring packing 9 (such as Cu packing) and a compression molded graphite ring 10. Thus, the length of the heater 7 that can project into the inside of the element 1 is regulated by the flange 8a of the pipe 8. The heater 7 is also sheathed with another metallic pipe 11. Provided around the pipe 11 is an insulator 12 made from alumina or the like. A coil spring 13 is deposited between said insulator 12 and pipe 11 to press the flanged portion 8a of the pipe 8. A metallic cover 14 is fitted on the open end side of the element 1, with an end of said cover 14 being in contact with the lead wire 5 at the top face of the annular enlarged portion 1a of the element 1. The other end of said cover 14 is caulked to a silicone rubber made ring spacer 15 secured on the outside of said pipe 11. Denoted by numeral 16 is a metallic cylindrical housing which is so designed that the element 1 rests on an interior annular seat 16a through a ring packing 17. Disposed between a section of the element 1 above its annular enlarged portion 1a and said housing 16 are a compression molded ring talc 18, an asbestos ring 19 and a heat-resistant metallic ring 20. Another insulator 21 made from alumina or other material is provided around said cover 14, and a cylindrical metallic protective cover 22 is mounted around said insulator 21.

A part of said insulator 21 and a part of said protective cover 22 are passed into the inside of the housing 16, and the upper end of said housing 16 is secured in position by a metallic caulking ring 23 fixed to an upper part of said housing 20. A lead wire 24 is welded at its terminal 24a to said cover 14. Another lead wire 25 is also welded at its terminal 25a to said pipe 11. A rubber tube 26 is securely caulked in position by a metallic collar 27. Numerals 28 and 29 indicate the terminals of said heater wire 7a. Numeral 30 denotes a fitting flange having a fitting hole 30a, 31 a protective cover having holes 31a, and 32 a rubber bush.

With the above-described arrangements, the electrode 3 is electrically connected to the lead wire 24 through lead wire 5 and cover 14 while the electrode 2 is electrically connected to the lead wire 25 through packing 9, ring 10 and pipes 8 and 11.

The oxygen analyzer according to this invention having the above-described structural arrangements is further described below from its operational aspect.

Lead wire 25 is connected to the positive pole (+) of the power source and lead wire 24 to the negative pole (−) and a voltage is applied across the two electrodes, whereupon an electric current flows from electrode 3 to electrode 2. Since the element 1 is an oxygen ion conductive solid electrolyte, oxygen existing in the gas to be analyzed migrates through the layer 4 to reach the electrode 3 where it is charged with electrons to turn into oxygen ions. These oxygen ions diffuse through the inside of the element 1, and upon reaching the electrode 2, they release electrons to return to oxygen molecules.

The oxygen molecules pass the through-hole 8b of the pipe 8 and are released into the atmosphere from the spaces between the respective component parts.

In this reaction, if the gas-diffusive resistive layer 4 is given a thickness greater than a certain value, for example 200 microns, with the electrode 3 being provided with a small surface area such as substantially 40 mm2, and the voltage is elevated gradually, there presents itself a region where, under the influence of said layer 4, the electric current remains unchanged even if the voltage is varied, that is, a limiting current is generated. This limiting current $I_l$ is given by the formula (1) as mentioned previously. Since the value of this limiting current varies according to the oxygen concentration (partial pressure) in the gas to be analyzed, it is possible to determine the partial pressure of oxygen in the gas by applying a given voltage and measuring said limiting current.

For explaining the present invention in a more definite way, there are shown below the test results in an embodiment of this invention, such embodiment being however merely intended to be illustrative and not restrictive to the scope of the invention.

EXAMPLE

Figure 3:
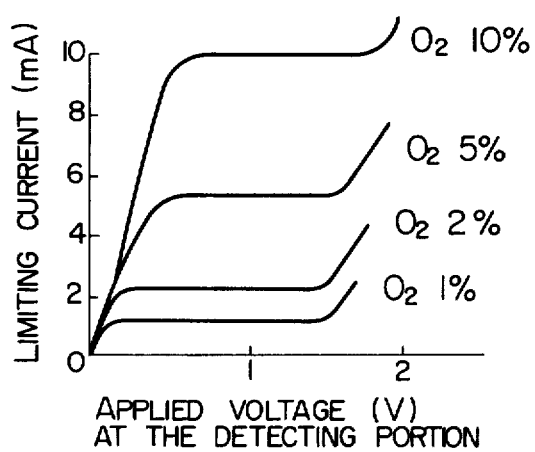
FIGS. 3 and 4 are the characteristic diagrams for explaining the operation of the oxygen analyzer according to this invention.
Figure 4:
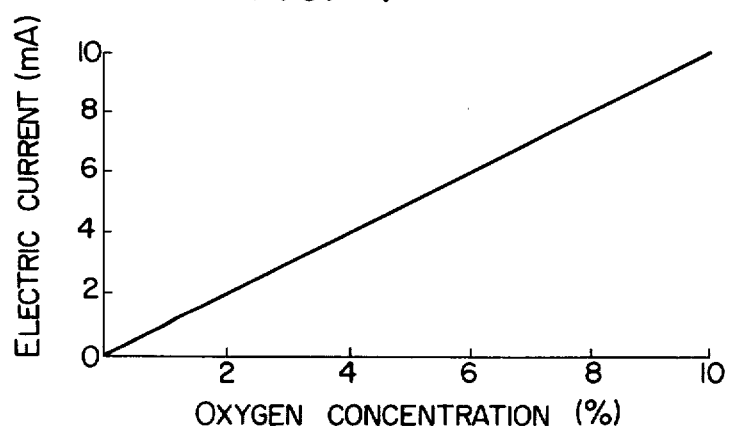

Measurement was made with the sensor shown in the accompanying drawings by using an $O_2$–$N_2$ type model gas at 75° C. With Run No. 4 mentioned later being taken for instance, it is seen that as the voltage is applied to the sensor, there comes out a region where the electric current remains substantially unchanged with increase of applied voltage in the range of about 0.3 to 1.5 V, and when the applied voltage is further increased, the electric current begins to rise up again as shown in FIG. 3. The current in this region is the limiting current, and the value of this limiting current varies according to the oxygen concentration in obedience to the above-shown formula (1). FIG. 4 shows the relation between oxygen concentration and limiting current when a given voltage (0.8 V) was applied. In this example, the temperature of the gas to be analyzed is 750° C. It is seen that the limiting current varies in proportion to the oxygen concentration, so that, for example, in application of the device to an internal combustion engine for automobile, it is possible to control the air/fuel ratio on the suction side of the engine by measuring the amperage of said limiting current to determine the residual oxygen concentration in the exhaust gas. In practical operations, the temperature of the gas to be analyzed is variable, causing a corresponding change of the limiting current, so that an electric current is applied to the heater wire 7a to keep the temperature of the element 1 constant.

Figure 6:
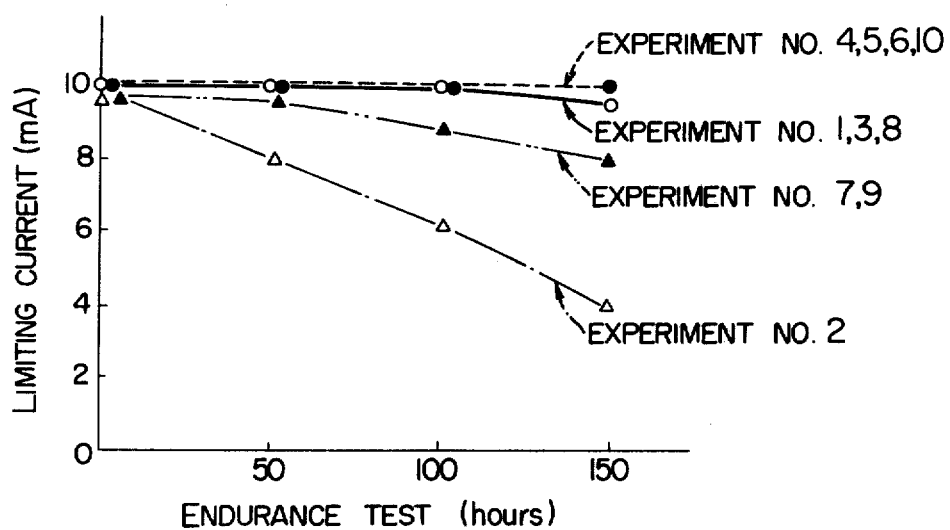

We have further conducted the experiments to see how the oxygen analyzer characteristics change with variation of porosity of the first, second and third layer 4a, 4b and 4c of said gas-diffusive resistive layer structure 4. Such experiments and the results thereof are explained below. Table 1 shows the relation between porosity of said respective layers and analyzer characteristics, and the determined characteristics shown in Table 1 are represented graphically in FIGS. 5 and 6. The measurements were made under the conditions of 750° C. gas temperature and 10% oxygen concentration.

serve as a deposit trapper and collects the deposits heavily, resulting in poor gas diffusion and a wide variation of limiting current (by a figure of about 20%) after the endurance test as in the case of Run Nos. 7 and 9 in FIG. 6. If said porosity is less than 15%, although deposition of the layer is lessened, there takes place intrusion of the deposits into the layer, causing a wide variation of limiting current as represented by Run No. 2. Accordingly, the porosity of the third layer should be within the range of 15 to 20%, with the average pore diameter being preferably from 1,200 to 1,500 Å.

The endurance test was conducted with a lean gas-burning system at 750° C. for 150 hours by using a commercially available 6-cylinder engine with a piston displacement of 2,000 cc for measuring the oxygen concentration over the range of 0 to 10%. FIG. 6 shows the results of measurements of the limiting current in the analyzer as measured at intervals of 50 hours in said 150-hour endurance test with a gas of 750° C. and 10% oxygen concentration.

Regarding the materials to be used for the first to third layers 4a-4c, it is desirable that the first layer 4a be made from a $ZrO_2$ type material in view of coefficient of thermal expansion with the solid electrolyte element 1, and it is most preferred to use a material of the same

TABLE 1

| | Porosity (%) Run No. | | | | | | | | | |
|---|---|---|---|---|---|---|---|---|---|---|
| | 1 | 2 | 3 | 4 | 5 | 6 | 7 | 8 | 9 | 10 |
| First layer (4a) $ZrO_2$ layer | 9.0 | 10.3 | 10.8 | 11.2 | 12.5 | 13.3 | 14.2 | 14.6 | 15.6 | 17.2 |
| Second layer (4b) $MgO \cdot Al_2O_3$ layer | 6.2 | 5.6 | 5.4 | 6.9 | 7.2 | 8.5 | 9.3 | 7.2 | 7.2 | 7.0 |
| Third layer (4c) $Al_2O_3$ layer | 15.3 | 14.0 | 18.2 | 16.8 | 16.3 | 19.1 | 20.9 | 19.7 | 21.0 | 17.8 |
| Initial characteristics (Sensor sharpness) | o | x | x | o | o | o | x | x | o | o |
| Adhesiveness of gas-diffusive resistive layer to electrodes | x | x | Δ | o | o | o | o | o | Δ | x |
| Change of limiting current in long-time use (due to clogging by deposits on composite layer) | Δ | x | o | o | o | o | x | Δ | x | o |

(Note)
o = good, Δ = fair, x = poor.

Figure 5:
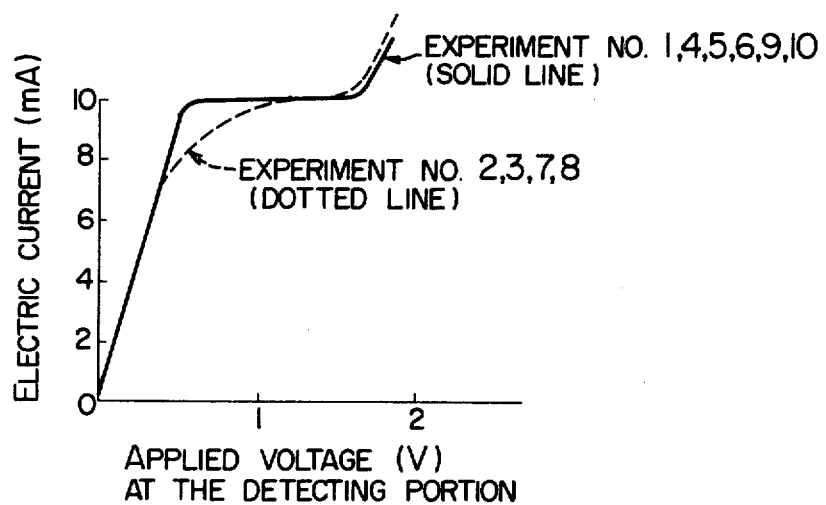
FIGS. 5 and 6 are the characteristic diagrams for explaining the effect of the oxygen analyzer according to this invention.

As seen from FIG. 5, if the porosity of the second layer 4b of lower than 6% or higher than 8%, no sharpness is provided in the limiting current characteristic and the current strength fluctuates widely according to the oxygen concentration for the reasons that pore continuity is lost if said porosity is lower than 6% and a film allowing uniform gas diffusion is not formed because of too high porosity if the porosity of said layer is higher than 8%. Thus, the porosity of the second layer 4b should be within the range of 6-8%. Also, the average pore diameter of the film is preferably 500 to 800 Å.

It is also seen from Table 1 that if the porosity of the first layer 4a is less than 11%, said layer proves to be too dense to serve as a cushioning medium, while if said porosity is greater than 15%, the layer proves to be too porous, resulting in poor adhesiveness to the electrode 3. This indicates that the porosity of greater than 15% leads to poor initial adhesive strength while the porosity of less than 11% leads to poor adhesive strength after long-time use. Thus, the first layer 4a is required to have a porosity of from 11 to 15%.

As for the porosity of the third layer 4c, if this porosity is above 20%, the layer proves to be too porous to composition as said element 1. The material for the second and third layer 4b and 4c may be properly selected from $Al_2O_3$, $MgO \cdot Al_2O_3$, $Al_2O_3 - TiO_2$, $ZrO_2$ and the like for providing the optimal porosity from the viewpoint of thermal expansion.

Further, the first to third layers 4a-4c of the gas-diffusive resistive layer structure 4 may be formed as ceramic filters by a sintering method, and bonding of these layers may be accomplished by sintering while bonding thereof to the electrode 3 may be effected by using a porous $ZrO_2$ type adhesive.

The element 1 may not necessarily be shaped into a cup-like configuration; it may be configured like a pellet, in which case the electrodes provided on both inner and outer sides of the element are exposed to the gas to be analyzed. In case the element is of such configuration, the gas-diffusive resistive layer of the three-layer structure according to this invention is provided on one of the electrodes and a porous protective layer made from a heat-resistant metal oxide of a single-layer structure is provided on the other electrode.

The present invention can be also applied for the detection of oxygen concentration in exhaust gas from ordinary combustion apparatus.

As described above in detail, according to the present invention, the gas-diffusive resistive layer provided on the electrode(s) of the solid electrolyte element is composed of a three-layer structure characterized by selection of the optimal porosities for the respective component layers (first, second and third layers counted from the electrode side), that is, the first layer has a porosity of 11–15%, the second layer 6–8%, and the third layer 15–20%, whereby it is possible to prevent clogging of said composite diffusive layer by the fine particles in the gas to be analyzed and thereby to minimize the fluctuation of the limiting current in long-time use without impairing adhesiveness of said composite layer to the electrode as well as sharpness of the sensor in sensing the limiting current behavior in relation to oxygen concentration.

What is claimed is:

1. A limiting current type oxygen analyzer designed for detecting oxygen concentration in a gas to be analyzed, comprising a solid electrolyte element made from an oxygen ion conductive metal oxide and a pair of porous film electrodes provided on the inner and outer sides of said element respectively, at least one of said electrodes being coated with a gas-diffusive resistive layer made from a porous insulating metal oxide, wherein the oxygen ions in the gas to which said element is exposed are caused to diffuse in the inside of said solid electrolyte element by applying a given voltage across said both electrodes and the limiting current corresponding to the concentration of said diffused oxygen ions is measured to determine the oxygen concentration in the gas to be analyzed, further characterized in that said gas-diffusive resistive layer is composed of a three-layer structure consisting of the first, second and third layers counted from the electrode side, said first layer having a porosity of 11–15%, the second layer 6–8% and the third layer 15–20%.

2. The oxygen analyzer according to claim 1, wherein the material constituting the first layer of said gas-diffusive resistive layer is $ZrO_2$.

3. The oxygen analyzer according to claim 1, wherein the material constituting the second and third layers of said gas-diffusive resistive layer is selected from the group consisting of $Al_2O_3$, $MgO\text{-}Al_2O_3$, $Al_2O_3\text{-}TiO_2$ and $ZrO_2$.

4. The oxygen analyzer according to claim 1, wherein the first layer of said gas-diffusive resistive layer has a thickness of 20–50 $\mu$, the second layer has a thickness of 130–160 $\mu$ and the third layer has a thickness of about 20 $\mu$, and the overall thickness of the gas-diffusive resistive layer is about 200 $\mu$.

* * * * *